United States Patent
Boylan et al.

(10) Patent No.: US 8,016,854 B2
(45) Date of Patent: *Sep. 13, 2011

(54) VARIABLE THICKNESS EMBOLIC FILTERING DEVICES AND METHODS OF MANUFACTURING THE SAME

(75) Inventors: John F. Boylan, Murrieta, CA (US); Orlando M. Padilla, Aliso Viejo, CA (US); Christopher J. Tarapata, North Andover, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 833 days.

This patent is subject to a terminal disclaimer.

(21) Appl. No.: 12/025,319

(22) Filed: Feb. 4, 2008

(65) Prior Publication Data

US 2008/0208244 A1    Aug. 28, 2008

Related U.S. Application Data

(63) Continuation of application No. 09/896,932, filed on Jun. 29, 2001, now Pat. No. 7,338,510.

(51) Int. Cl.
*A61M 29/00* (2006.01)
(52) U.S. Cl. .................. 606/200; 623/1.11
(58) Field of Classification Search ............ 606/195, 606/198, 200, 159, 113, 114; 623/1.11, 1.15, 623/1.23; 604/96.01, 103.01
See application file for complete search history.

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |

(Continued)

FOREIGN PATENT DOCUMENTS

EP    0427429 A3    9/1991

(Continued)

OTHER PUBLICATIONS

Dilitation of the Carotid Artery by a Temporary Carotid Filter by A. Beck, St. Milic, A.M. Spagnoli, Nov.-Dec. Issue of Oplitai, An International Journal on Military Medicine and Health Emergencies, pp. 67-74.

(Continued)

*Primary Examiner* — Victor Nguyen
(74) *Attorney, Agent, or Firm* — Fulwider Patton LLP; Jonathan Feuchtwang

(57) ABSTRACT

A strut assembly to be used in conjunction with an embolic filtering device has varying strut thicknesses, with the thickness selected based at least in part on the flexing characteristics of the particular portion of the strut assembly. The strut assembly is formed with patterns having flexing portions and stable portions, with the flexing portions contributing to the flexibility of the strut assembly during delivery and recovery in the patient's vasculature. The stable portions remain relatively unflexed and stiff when being delivered or recovered from the patient's vasculature. The stable portions provide strength and increased radiopacity to the strut assembly which is needed when the strut assembly is deployed in the body vessel. The flexing portions act much like a mechanical hinges in providing the needed flexibility to resiliently bend when being delivered through tortuous anatomy of the patient.

17 Claims, 5 Drawing Sheets

U.S. PATENT DOCUMENTS

| | | |
|---|---|---|
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,662,703 A | 9/1997 | Yurek et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,776,183 A * | 7/1998 | Kanesaka et al. ............ 623/1.15 |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |

| | | |
|---|---|---|
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,364,900 B1 | 4/2002 | Heuser |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 * | 3/2003 | Boyle et al. ............ 606/200 |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Weber et al. |
| 6,699,260 B2 | 3/2004 | Dubrul et al. |
| 6,702,834 B1 | 3/2004 | Boyle et al. |
| 6,706,055 B2 | 3/2004 | Douk et al. |

| Patent | Date | Inventor |
|---|---|---|
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews et al. |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi et al. |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi et al. |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Davis et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |

| | | | | | | |
|---|---|---|---|---|---|---|
| 2003/0004541 A1 | 1/2003 | Linder et al. | | 2003/0212429 A1 | 11/2003 | Keegan et al. |
| 2003/0009188 A1 | 1/2003 | Linder et al. | | 2003/0212431 A1 | 11/2003 | Brady et al. |
| 2003/0009189 A1 | 1/2003 | Gilson et al. | | 2003/0212434 A1 | 11/2003 | Thielen |
| 2003/0015206 A1 | 1/2003 | Roth et al. | | 2003/0216774 A1 | 11/2003 | Larson |
| 2003/0018354 A1 | 1/2003 | Roth et al. | | 2003/0220665 A1 | 11/2003 | Eskuri et al. |
| 2003/0023265 A1 | 1/2003 | Forber | | 2003/0225418 A1 | 12/2003 | Eskuri et al. |
| 2003/0028238 A1 | 2/2003 | Burkett et al. | | 2003/0225435 A1 | 12/2003 | Huter et al. |
| 2003/0032941 A1 | 2/2003 | Boyle et al. | | 2003/0229295 A1 | 12/2003 | Houde et al. |
| 2003/0032977 A1 | 2/2003 | Brady | | 2003/0229374 A1 | 12/2003 | Brady et al. |
| 2003/0040772 A1 | 2/2003 | Hyodoh et al. | | 2003/0233117 A1 | 12/2003 | Adams et al. |
| 2003/0042186 A1 | 3/2003 | Boyle | | 2003/0236545 A1 | 12/2003 | Gilson |
| 2003/0045898 A1 | 3/2003 | Harrison et al. | | 2004/0002730 A1 | 1/2004 | Denison et al. |
| 2003/0057156 A1 | 3/2003 | Peterson et al. | | 2004/0006361 A1 | 1/2004 | Boyle et al. |
| 2003/0060782 A1 | 3/2003 | Bose et al. | | 2004/0006364 A1 | 1/2004 | Ladd |
| 2003/0060843 A1 | 3/2003 | Boucher | | 2004/0006365 A1 | 1/2004 | Brady et al. |
| 2003/0060844 A1 | 3/2003 | Borillo et al. | | 2004/0006366 A1 | 1/2004 | Huter et al. |
| 2003/0065354 A1 | 4/2003 | Boyle et al. | | 2004/0006367 A1 | 1/2004 | Johnson et al. |
| 2003/0069596 A1 | 4/2003 | Eskuri | | 2004/0006368 A1 | 1/2004 | Mazzocchi et al. |
| 2003/0069597 A1 | 4/2003 | Petersen | | 2004/0015184 A1 | 1/2004 | Boyle et al. |
| 2003/0078519 A1 | 4/2003 | Salahieh et al. | | 2004/0019363 A1 | 1/2004 | Hanson et al. |
| 2003/0078614 A1 | 4/2003 | Satahieh et al. | | 2004/0034385 A1 | 2/2004 | Gilson et al. |
| 2003/0083692 A1 | 5/2003 | Vrba et al. | | 2004/0039411 A1 | 2/2004 | Gilson et al. |
| 2003/0083693 A1 | 5/2003 | Daniel et al. | | 2004/0044359 A1 | 3/2004 | Renati et al. |
| 2003/0097095 A1 | 5/2003 | Brady et al. | | 2004/0044360 A1 | 3/2004 | Lowe |
| 2003/0100917 A1 | 5/2003 | Boyle et al. | | 2004/0049226 A1 | 3/2004 | Keegan et al. |
| 2003/0100918 A1 | 5/2003 | Duane | | 2004/0059372 A1 | 3/2004 | Tsugita |
| 2003/0105484 A1 | 6/2003 | Boyle et al. | | 2004/0059373 A1 | 3/2004 | Shapiro et al. |
| 2003/0109824 A1 | 6/2003 | Anderson et al. | | 2004/0082967 A1 | 4/2004 | Broome et al. |
| 2003/0114879 A1 | 6/2003 | Euteneuer et al. | | 2004/0082968 A1 | 4/2004 | Krolik et al. |
| 2003/0114880 A1 | 6/2003 | Hansen et al. | | 2004/0088000 A1 | 5/2004 | Muller |
| 2003/0120303 A1 | 6/2003 | Boyle et al. | | 2004/0088002 A1 | 5/2004 | Boyle et al. |
| 2003/0125764 A1 | 7/2003 | Brady et al. | | 2004/0093009 A1 | 5/2004 | Denison et al. |
| 2003/0130680 A1 | 7/2003 | Russell | | 2004/0093010 A1 | 5/2004 | Gesswein et al. |
| 2003/0130681 A1 | 7/2003 | Ungs | | 2004/0093011 A1 | 5/2004 | Vrba |
| 2003/0130682 A1 | 7/2003 | Broome et al. | | 2004/0093012 A1 | 5/2004 | Cully et al. |
| 2003/0130684 A1 | 7/2003 | Brady et al. | | 2004/0093013 A1 | 5/2004 | Brady et al. |
| 2003/0130685 A1 | 7/2003 | Daniel et al. | | 2004/0098022 A1 | 5/2004 | Barone |
| 2003/0130686 A1 | 7/2003 | Daniel et al. | | 2004/0098026 A1 | 5/2004 | Joergensen et al. |
| 2003/0130687 A1 | 7/2003 | Daniel et al. | | 2004/0098032 A1 | 5/2004 | Papp et al. |
| 2003/0130688 A1 | 7/2003 | Daniel et al. | | 2004/0098033 A1 | 5/2004 | Leeflang et al. |
| 2003/0135162 A1 | 7/2003 | Deyette, Jr. et al. | | 2004/0102807 A1 | 5/2004 | Kusleika et al. |
| 2003/0135232 A1 | 7/2003 | Douk et al. | | 2004/0106944 A1 | 6/2004 | Daniel et al. |
| 2003/0139764 A1 | 7/2003 | Levinson et al. | | 2004/0111111 A1 | 6/2004 | Lin |
| 2003/0144685 A1 | 7/2003 | Boyle et al. | | 2004/0116960 A1 | 6/2004 | Demond et al. |
| 2003/0144689 A1 | 7/2003 | Brady et al. | | 2004/0122466 A1 | 6/2004 | Bales |
| 2003/0150821 A1 | 8/2003 | Bates et al. | | 2004/0127933 A1 | 7/2004 | Demond et al. |
| 2003/0153935 A1 | 8/2003 | Mialhe | | 2004/0127934 A1 | 7/2004 | Gilson et al. |
| 2003/0153942 A1 | 8/2003 | Wang et al. | | 2004/0127936 A1 | 7/2004 | Salahieh et al. |
| 2003/0153943 A1 | 8/2003 | Michael et al. | | 2004/0138693 A1 | 7/2004 | Eskuri et al. |
| 2003/0158574 A1 | 8/2003 | Esch et al. | | 2004/0138694 A1 | 7/2004 | Tran et al. |
| 2003/0163064 A1 | 8/2003 | Vrba et al. | | 2004/0138696 A1 | 7/2004 | Drasler et al. |
| 2003/0171770 A1 | 9/2003 | Kusleika et al. | | 2004/0147955 A1 | 7/2004 | Beulke et al. |
| 2003/0171771 A1 | 9/2003 | Anderson et al. | | 2004/0153118 A1 | 8/2004 | Clubb et al. |
| 2003/0171803 A1 | 9/2003 | Shimon | | 2004/0153119 A1 | 8/2004 | Kusleika et al. |
| 2003/0176884 A1 | 9/2003 | Berrada et al. | | 2004/0158275 A1 | 8/2004 | Crank et al. |
| 2003/0176885 A1 | 9/2003 | Broome et al. | | 2004/0158277 A1 | 8/2004 | Lowe et al. |
| 2003/0176886 A1 | 9/2003 | Wholey et al. | | 2004/0158278 A1 | 8/2004 | Becker et al. |
| 2003/0176889 A1 | 9/2003 | Boyle et al. | | 2004/0158279 A1 | 8/2004 | Petersen |
| 2003/0181942 A1 | 9/2003 | Sutton et al. | | 2004/0158280 A1 | 8/2004 | Morris et al. |
| 2003/0181943 A1 | 9/2003 | Daniel et al. | | 2004/0158281 A1 | 8/2004 | Boylan et al. |
| 2003/0187474 A1 | 10/2003 | Keegan et al. | | 2004/0167564 A1 | 8/2004 | Fedie |
| 2003/0187475 A1 | 10/2003 | Tsugita et al. | | 2004/0167565 A1 | 8/2004 | Beulke et al. |
| 2003/0187495 A1 | 10/2003 | Cully et al. | | 2004/0167566 A1 | 8/2004 | Beulke et al. |
| 2003/0191493 A1 | 10/2003 | Epstein et al. | | 2004/0167567 A1 | 8/2004 | Cano et al. |
| 2003/0195554 A1 | 10/2003 | Shen et al. | | 2004/0167568 A1 | 8/2004 | Boylan et al. |
| 2003/0195555 A1 | 10/2003 | Khairkhahan et al. | | 2004/0172055 A1 | 9/2004 | Huter et al. |
| 2003/0195556 A1 | 10/2003 | Stack et al. | | 2004/0176794 A1 | 9/2004 | Khosravi |
| 2003/0199819 A1 | 10/2003 | Beck | | 2004/0193208 A1 | 9/2004 | Talpade et al. |
| 2003/0199921 A1 | 10/2003 | Palmer et al. | | 2004/0199198 A1 | 10/2004 | Beulke et al. |
| 2003/0204168 A1 | 10/2003 | Bosme et al. | | 2004/0199199 A1 | 10/2004 | Krolik et al. |
| 2003/0204202 A1 | 10/2003 | Palmer et al. | | 2004/0199203 A1 | 10/2004 | Oslund et al. |
| 2003/0208222 A1 | 11/2003 | Zadno-Azizi | | 2004/0204737 A1 | 10/2004 | Boismier et al. |
| 2003/0208224 A1 | 11/2003 | Broome | | 2004/0210250 A1 | 10/2004 | Eskuri |
| 2003/0208225 A1 | 11/2003 | Goll et al. | | 2004/0220608 A1 | 11/2004 | D'Aquanni et al. |
| 2003/0208226 A1 | 11/2003 | Bruckheimer et al. | | 2004/0220609 A1 | 11/2004 | Douk et al. |
| 2003/0208227 A1 | 11/2003 | Thomas | | 2004/0220611 A1 | 11/2004 | Ogle |
| 2003/0208228 A1 | 11/2003 | Gilson et al. | | 2004/0225322 A1 | 11/2004 | Garrison et al. |
| 2003/0208229 A1 | 11/2003 | Kletschka | | 2004/0236368 A1 | 11/2004 | McGucklin, Jr. et al. |
| 2003/0212361 A1 | 11/2003 | Boyle et al. | | 2004/0236369 A1 | 11/2004 | Dubrul |

| Publication No. | Date | Inventor |
|---|---|---|
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO 98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO02/28292 | 4/2002 |
| WO | WO2004/021928 | 3/2004 |

OTHER PUBLICATIONS

Minibasket for Percutaneous Embolectomy and Filter ProtectionAgainst Distal Embolization: Technical Note.

* cited by examiner

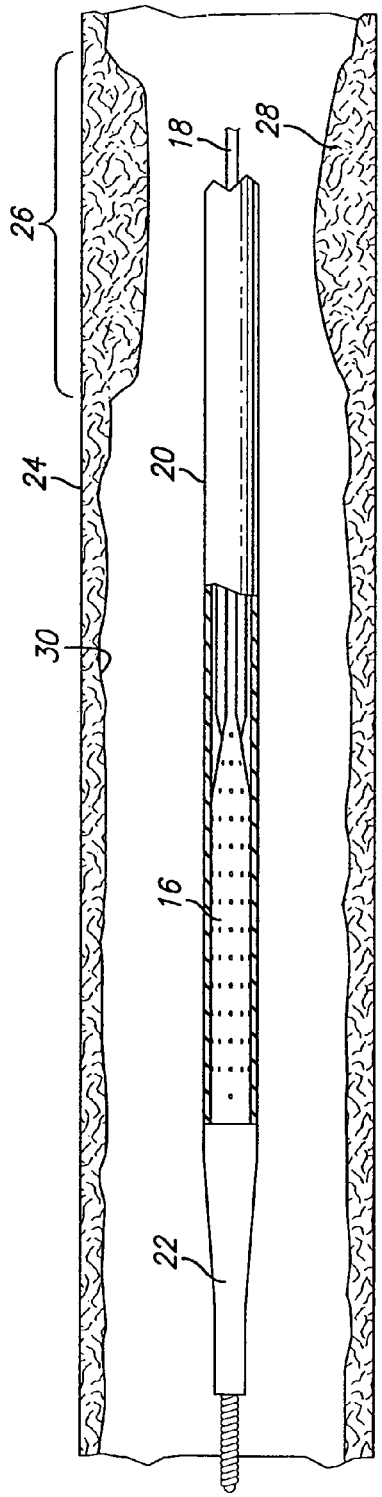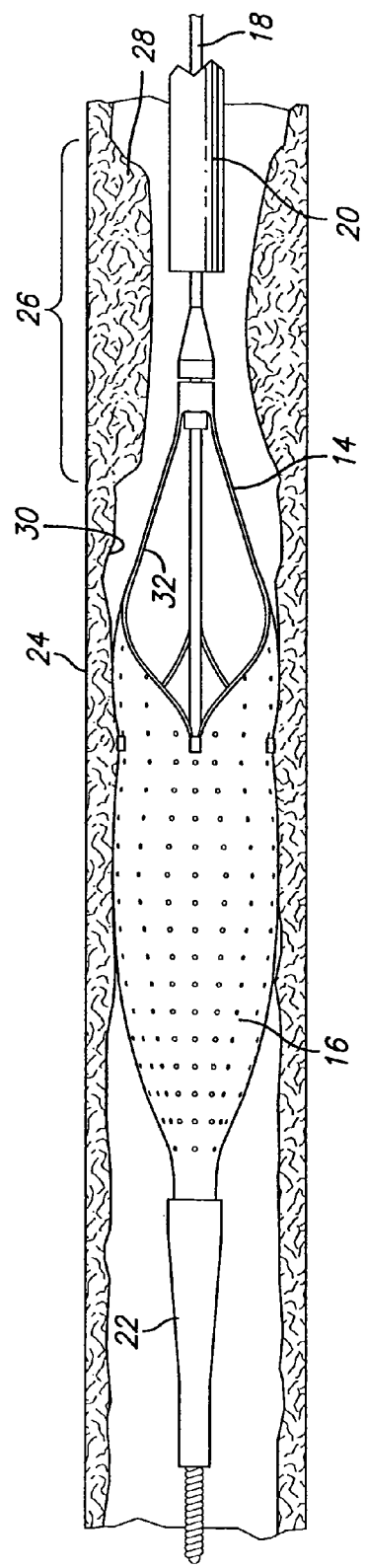

VARIABLE THICKNESS EMBOLIC FILTERING DEVICES AND METHODS OF MANUFACTURING THE SAME

CROSS-REFERENCE TO RELATED APPLICATIONS

This is a continuation of U.S. Ser. No. 09/896,932, filed Jun. 29, 2001, which issued as U. S. Pat. No. 7,338,510 on Mar. 4, 2008, the contents of which are hereby incorporated by reference.

BACKGROUND OF THE INVENTION

The present invention relates generally to filtering devices and systems which can be used when an interventional procedure is being performed in a stenosed or occluded region of a body vessel to capture embolic material that may be created and released into the vessel during the procedure. The present invention is more particularly directed to an embolic filtering device with a strut assembly having varying wall thickness and strut widths. The present invention is particularly useful when an interventional procedure, such as balloon angioplasty, stenting procedures, laser angioplasty or atherectomy, is being performed in a critical body vessel, such as the carotid arteries, where the release of embolic debris into the bloodstream can occlude the flow of oxygenated blood to the brain, resulting in grave consequences to the patient. While the present invention is particularly useful in carotid procedures, the invention can be used in conjunction with any vascular interventional procedure in which an embolic risk is present.

Numerous procedures have been developed for treating occluded blood vessels to allow blood to flow without obstruction. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during laser angioplasty, sometimes particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the vacuum catheter does not remove all of the embolic material from the bloodstream. Also, a powerful suction could cause trauma to the patient's vasculature.

Still other techniques which have had some limited success include the placement of a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel. Additionally, the recovery apparatus should be relatively flexible to avoid straightening of the body vessel. Recovery devices which are too stiff can cause trauma to the vessel walls as the filter is being collapsed and removed from the vasculature.

Some prior art expandable filters are attached to the distal end of a guide wire or guide wire-like tubing that allows the filtering device to be placed in the patient's vasculature as the guide wire is steered by the physician. Once the guide wire is in proper position in the vasculature, the embolic filter can be deployed to capture embolic debris. Some embolic filter devices which utilize a guide wire for positioning also utilize the restraining sheath to maintain the expandable filter in a collapsed position. Once the proximal end of the restraining sheath is retracted by the physician, the expandable filter will move into its fully expanded position within the patient's vasculature. The restraining sheath can then be removed from the guide wire allowing the guide wire to be used by the physician to deliver interventional devices, such as a balloon angioplasty dilatation catheter or a stent delivery catheter, into the area of treatment. After the interventional procedure is completed, a recovery sheath can be delivered over the guide wire using over-the-wire techniques to collapse the expanded filter for removal from the patient's vasculature. As mentioned above, the recovery device, i.e., the recovery sheath, should be relatively flexible to track over the guide wire and to avoid straightening the body vessel once it is in place.

When a combination of an expandable filter and guide wire is utilized, it is important that the expandable filter remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Additionally, a fluoroscope is currently the most widely used instrument to visualize the filter during deployment and as such, requires an expandable filter having sufficient radiopacity to produce an identifiable image.

Expandable filters can be provided with high flexibility by forming the struts of the filter assembly from relatively thin material. However, the use of thin material often can reduce the radiopacity of the expandable filter, often making it difficult for the physician to visualize the filter during deployment. Conversely, the use of thicker materials, which can promote radiopacity of the expandable filter, usually reduces its flexibility, which may impair the deliverability of the expandable filter within the patient. Since some expandable filter assemblies are made from nickel titanium alloys, which provide the self-expansion characteristics to the filter assembly, there may be a need for increasing radiopacity since nickel titanium generally has a low degree of radiopacity. Moreover, the radiopacity of an expandable filtering assembly which utilizes nickel titanium can be greatly reduced if the struts of the filter assembly are formed thinner in order to increase the flexibility of the filter assembly. Therefore, there is a need for a careful balance between achieving high flexibility in the filter assembly while maintaining sufficient radiopacity to allow the device to be visualized using current visualization equipment. What has been needed is an expandable filter assembly having high flexibility with sufficient strength and radiopacity to be successfully deployed within a patient's vasculature to collect embolic debris which may be released into the patient's vasculature. The present invention disclosed herein satisfies these and other needs.

SUMMARY OF THE INVENTION

The present invention provides an expandable strut assembly and methods for making the same which can be used to create an embolic filtering device for capturing embolic debris created during the performance of a therapeutic interventional procedure, such as a balloon angioplasty or stenting procedure, in a body vessel. The present invention is particularly useful when an interventional procedure is being performed in critical arteries, such as the carotid arteries, in which vital downstream blood vessels can easily become blocked with embolic debris, including the main blood vessels leading to the brain. The present invention provides the physician with a flexible embolic filtering device which is sufficiently flexible to be steered through tortuous anatomy, but yet possesses sufficient strength to hold open a filtering element against the wall of the body vessel for capturing embolic debris. Moreover, the present invention provides sufficient flexibility without compromising the radiopacity characteristics of the filtering device. As a result, an embolic filtering device made in accordance with the present invention is relatively easy to deploy, has enhanced visibility under flouroscopy, and has good flexibility and conformable to the patient's anatomy.

An embolic filter assembly of the present invention utilizes an expandable strut assembly made from a self-expanding material, for example, nickel titanium (NiTi) or spring steel, and includes a number of outwardly extending struts capable of expanding from a collapsed position having a first delivery diameter to an expanded or deployed position having a second implanted diameter. A filter element made from an embolic-capturing material can be attached to the expandable strut assembly to move between the collapsed position and the deployed position with expandable struts.

The struts of the strut assembly can be set to remain in the expanded, deployed position until an external force is placed over the struts to collapse and move the struts to the collapsed position. One way of accomplishing this is through the use of a restraining sheath, for example, which can be placed over the filtering device in a coaxial fashion to contact the strut assembly and move the assembly into the collapsed position. The embolic filtering device can be implanted in the patient's vasculature and remain implanted for a period of time or can be attached to the distal end of an elongated member, such as a guide wire, for temporary placement in the vasculature. A guide wire is used in conjunction with the filtering device when embolic debris is to be filtered during an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the strut assembly into the expanded position. This can be easily performed by the physician by simply retracting the proximal end of the restraining sheath (located outside of the patient). Once the restraining sheath is retracted, the self-expanding properties of the strut assembly cause each strut to move in a outward, radial fashion away from the guide wire to contact the wall of the body vessel. As the struts expand radially, so does the filter element which will now be maintained in place to collect any embolic debris that may be released into the bloodstream as the physician performs the interventional procedure. The guide wire is used by the physician to deliver the necessary interventional device into the are of treatment. The deployed filter element captures embolic debris which may be created and released into the body vessel during the procedure.

The strut assembly which forms pare of the filtering assembly includes portions in which the struts flex during delivery and recovery of the device within the patient's vasculature. Also, there are portions of the strut assembly which will remain relatively stable (i.e., largely undeformed or not flexed) during the travel through the sometimes tortuous pathway of the patient's vasculature. For example, as the embolic filtering device is being delivered through the patient's vasculature, it will bend longitudinally in order to cross and navigate the curves of the vasculature. When the strut assembly passes through such curved portions of the vasculature, the flexing portions of the strut assembly will resiliently flex while the stable portions remain largely unflexed or undeformed, even when the filtering assembly as a whole is being delivered through extremely tight turns. Thus, the strut assembly of the embolic filtering assembly can be thought of having both flexing portions and stable portions which cooperate with each other in order to provide a composite assembly having both the necessary flexibility and strength to create an effective embolic filtering device.

The flexibility of the strut assembly is largely derived from those portion of the struts which actually flex, without substantial assistance from the stable portions of the assembly. Those stable portions are usually not subject to sufficient loads to cause bending when the composite device is delivered across curved portions of the anatomy since the flexing portions delivering the flexibility need to negotiate the turns. Accordingly, the stable portions of the strut assembly will remain substantially stiff and will not undergo substantial bending or flexing. As a result, these stable portions provide strength to the strut assembly which will be later needed when the strut assembly is expanded in the body vessel to maintain the filter element in its deployed position in the body vessel. Accordingly, the thickness or width of the stable portions of the strut assembly will not materially impact the overall flexibility or ease of delivering the embolic filtering assembly through the patient's vasculature.

The flexing portions of the strut assembly, on the other hand, can have reduced strut thickness or strut width to increase the strut assembly's overall ability to flex or bend as it is being delivered through the curved portions of the anatomy. Thus, in order to provide an optimal range of strength, flexibility and radiopacity, the present invention provides a strut assembly having thinner areas which promote flexibility, with greater strut thickness and/or widths in select stable areas to promote greater strength. This use of thicker and/or wider struts provides enhanced visibility by increasing the radiopacity in those select areas. By increasing the amount of material in the stable areas of the strut assembly, overall flexibility should not be impacted by the thicker or wider struts in the stable portions. On the other hand, a thinner and/or narrower strut can be utilized in the flexing portions to achieve the needed overall flexibility for the strut assembly. Again, the stable portions could utilize thicker struts or wider struts for increased radiopacity while the thinner, narrower struts in the flexing portions would create preferential bending points leading to enhanced conformability and flexibility.

Additionally, in embolic filtering devices which utilize a restraining sheath to deploy the self-expanding filter assembly, the surface area of the strut assembly in contact with the sheath can be decreased thereby reducing the amount of friction created between restraining sheath and strut assembly as the sheath is being retracted over the struts. As a result, it should be easier to retract the restraining sheath once the filter assembly is to be deployed in the patient's vasculature. The combination of these properties lead to an embolic filtering device which can be easy to deploy, is more visible under a fluoroscope, and has increased flexibility and conformability with the patient's anatomy. The present invention is also directed to various methods for making such an expandable strut assembly/filtering device.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 3 is an elevational view, partially in cross section, of an embolic filtering device embodying features of the present invention as it is initially being delivered past an area of treatment within a body vessel.

FIG. 4 is an elevational view, partially in cross section, similar to that shown in FIG. 3, wherein the embolic filtering device is deployed in its expanded, implanted position within the body vessel.

DETAILED DESCRIPTION OF THE PREFERRED EMBODIMENTS

Figure 1:
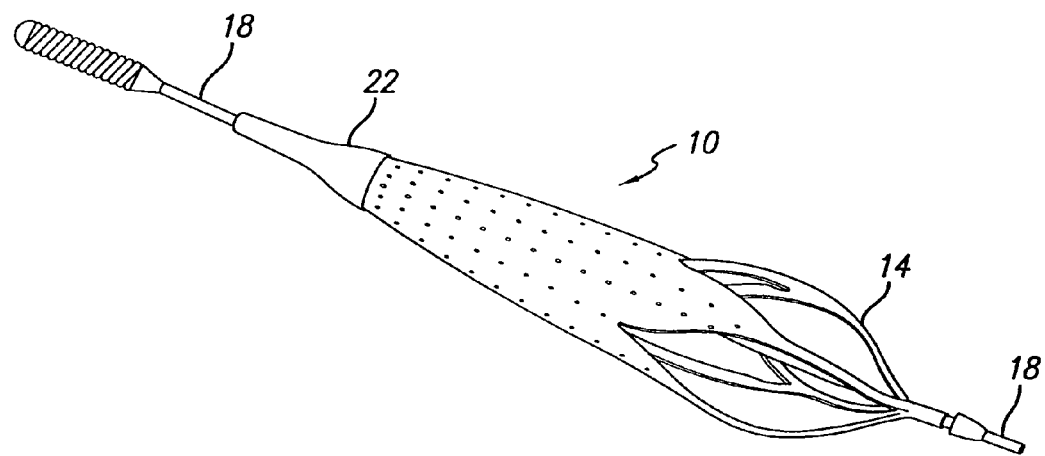
FIG. 1 is a perspective view of an embolic filtering device embodying features of the present invention.
Figure 2:
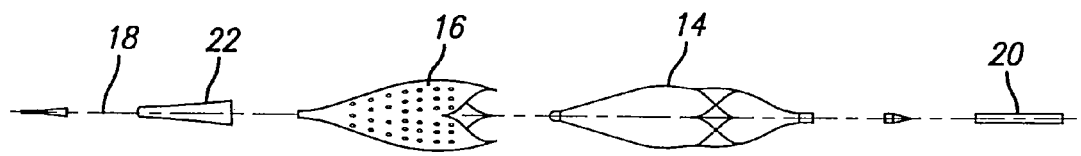
FIG. 2 is an elevational view of the various components making up the embodiment of the embolic filtering device shown in FIG. 1.
Figure 5:
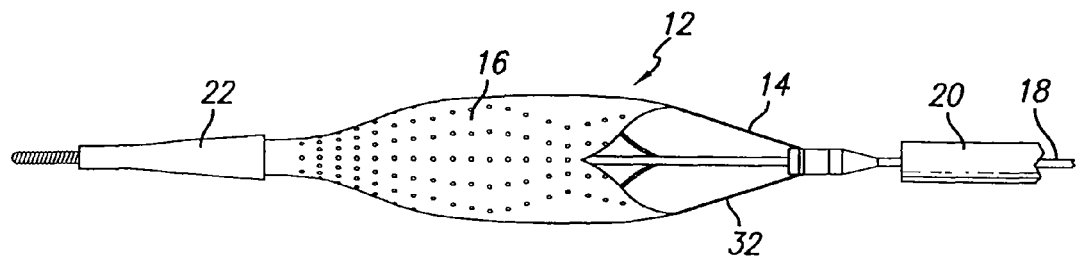
FIG. 5 is an elevational view of the embolic filtering device of FIG. 1.

Turning now to the drawings, in which like reference numerals represent like or corresponding elements in the drawings, FIGS. 1 and 2 illustrate one particular embodiment of an embolic filtering device 10 incorporating features of the present invention. This embolic filtering device 10 is designed to capture embolic debris which may be created and released into a body vessel during an interventional procedure. The embolic filtering device 10 includes an expandable filter assembly 12 having a self-expanding strut assembly 14 and a filter element 16 attached thereto. In this particular embodiment, the expandable filter assembly 12 is rotatably mounted on the distal end of an elongated tubular shaft, such as a steerable guide wire 18. A restraining or delivery sheath 20 (FIG. 3) extends coaxially along the guide wire 18 in order to maintain the expandable filter assembly 12 in its collapsed position until it is ready to be deployed within the patient's vasculature. The expandable filter assembly 12 is deployed by the physician by simply retracting the restraining sheath 20 proximally to expose the expandable filter assembly. The self-expanding strut assembly 14 thus becomes uncovered and immediately begins to expand within the body vessel (see FIG. 4).

It should be appreciated that the embolic filtering device 10 depicted herein is just one example of the numerous designs which can be used to create an embolic protection device made in accordance with the present invention. An obturator 22 affixed to the distal end of the filter assembly 12 can be implemented to prevent possible "snowplowing" of the embolic protection device as it is being delivered through the vasculature. The obturator can be made from a soft polymeric material, such as Pebax D 40, and has a smooth surface to help the embolic filtering device travel through the vasculature and cross lesions while preventing the distal end of the restraining sheath 20 from "digging" or "snowplowing" into the wall of the body vessel. Additional details regarding the particular structure and shape of the various elements making up the filter assembly 12 are provided below.

In FIG. 3, the embolic filtering device 10 is shown as it is being delivered within an artery 24 or other body vessel of the patient. This portion of the artery 24 has an area of treatment 26 in which atherosclerotic plaque 28 has built up against the inside wall 30 of the artery 24. The filter assembly 12 is to be placed distal to, and downstream from, the area of treatment 26 as is shown in FIGS. 3 and 4. The therapeutic interventional procedure may comprise the implantation of a stent (not shown) to increase the diameter of an occluded artery and increase the flow of blood therethrough. It should be appreciated that the embodiments of the embolic filtering device and method for manufacturing and using the same are illustrated and described herein by way of example only and not by way of limitation. Also, while the present invention is described in detail as applied to an artery of the patient, those skilled in the art will appreciate that it can also be used in other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The strut assembly 14 includes self-expanding struts 32 which, upon release from the restraining sheath 20, expand the filter element 16 into its deployed position within the artery (FIG. 4). When the struts 32 are expanded, the filter element 16 may take on a basket shape, or any other shape, that will adequately deploy the filter element 16 against the wall of the artery. Embolic debris created during the interventional procedure and released into the bloodstream are captured within the deployed filter element 16. Although not shown, a balloon angioplasty catheter can be initially introduced within the patient's vasculature in a conventional SELDINGER technique through a guiding catheter (not shown). The guide wire 18 is disposed through the area of treatment and the dilatation catheter can be advanced over the guide wire 18 within the artery 24 until the balloon portion is directly in the area of treatment 26. The balloon of the dilatation catheter can be expanded, expanding the plaque 28 against the inside wall 30 of the artery 24 to expand the artery and reduce the blockage in the vessel at the position of the plaque 28. After the dilatation catheter is removed from the patient's vasculature, a stent (not shown) could be implanted in the area of treatment 26 using over-the-wire techniques to help hold and maintain open this portion of the artery 24 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and should enter the filter 16. Once the procedure is completed, the interventional device is removed from the guide wire and the filter assembly 14 is to be collapsed and removed from the artery 24, taking with it any embolic debris trapped within the filter element 16. A recovery sheath (not shown) can be delivered over the guide wire 18 to collapse the filter assembly for removal from the patient's vasculature.

Figure 6:
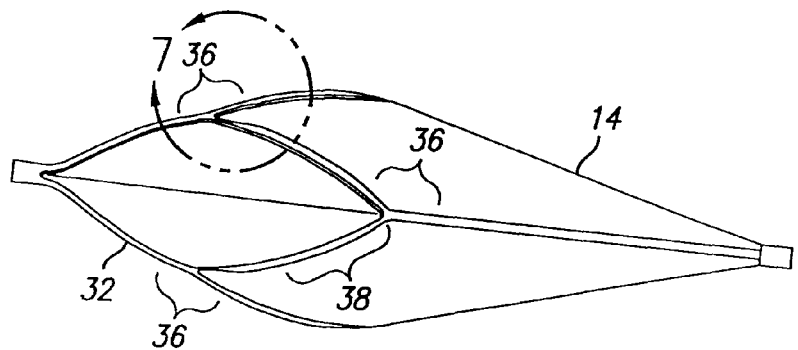
FIG. 6 is an elevational view of one embodiment of a strut assembly which can be used to form the embolic filtering device of FIGS. 1-4.
Figure 7:
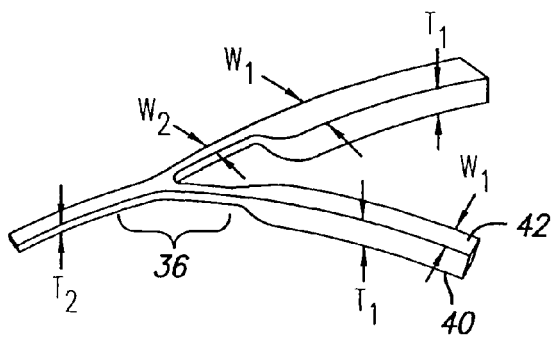
FIG. 7 is an elevational view, partially fragmented, of flexing portions of the strut assembly shown in FIG. 6.

The ability of the embolic filtering device to negotiate the sometime tortuous anatomy of the patient results from the flexibility associated with the strut assembly 14 which forms part of the filter assembly 12. Referring specifically now to FIGS. 6 and 7, one particular embodiment of a strut assembly 14 is shown which incorporates features of the present invention. It should be appreciated by those skilled in the art that this is just one particular structure incorporating struts which form a basket-like structure that can be used in accordance with the present invention. Many other structural designs could also be implemented to create the strut assembly without departing from the spirit and scope of the present invention.

The struts 32 which form the strut assembly 14 shown in FIGS. 6 and 7 include flexing portions 36 in which the struts or portions of the struts flex or otherwise resiliently bend both during delivery and recovery of the embolic filtering device. Also, there are stable portions 38 of the strut assembly which remain stable (i.e., largely undeformed or unflexed) during delivery through the vasculature. For example, as the embolic filtering device is being delivered through the patient's vasculature, it will bend longitudinally to cross and navigate the curves of the vasculature. When the strut assembly passes through such curved portions, the flexing portions 36 of the assembly will flex while the remaining portions stay relatively unflexed or stiff, even as the filtering assembly as a whole is bent through extremely tight turns. The flexing portions 36 and stable portions 38 thus cooperate with each other in order to provide the necessary flexibility to bend and be delivered through tight turns. The strength of the strut assembly 14 is achieved by the stable portions 38 once the strut assembly is deployed in the body vessel.

The flexibility of the strut assembly 14 is largely derived from the flexing portions 36 of the strut, without substantial assistance from the stable portions 38 of the assembly, even though stable portions 38 are subjected to some bending forces when the device is being delivered across curved portions of the anatomy. Accordingly, the stable portions 38 will remain substantially straight and will not undergo substantial bending or flexing. These stable portions 38 do have sufficient strength to provide the structural integrity needed to maintain the filter assembly 12 in its expanded position once placed in the artery. The strong stable portions 38 also provide additional metal to the strut assembly which allows the embolic filtering device 10 to become more visible utilizing equipment, such as a fluoroscope, to determine the location of the device within the patient's anatomy. As can be seen in FIGS. 6 and 7, the stable portions 38 include strut portions which have greater strut depth or thickness than the portion of the struts which are located in the flex portions 36. As can be seen specifically in FIG. 7, the thickness of the strut or the strut depth is the measurement of the strut from the inner surface 40 to the outer surface 42 of the strut. In FIG. 7, arrows $T_1$ show the greater strut thickness in the stable portions 38 which provides the higher strength and radiopacity than the strut thickness in the flex portions 36 (indicated by arrows $T_2$). The strut thickness in the flex portions 38 depicted by arrows $T_2$ is less than the strut thickness in the stable portion 36, thus providing increased flexibility to the strut assembly 14.

The stable portion 38 may also include struts which have greater strut widths than the struts which are located in the flexing portions 36 of the strut assembly 14. In FIG. 7, arrows $T_1$ show the wider strut formed in the stable portions 38. Arrows $T_2$ show the smaller strut widths appearing in the flexing portions 36. The smaller strut width provides greater flexibility, enhancing the ability of the strut assembly 14 to negotiate the tortuous anatomy of the patient. As a result, the flexing portions 36 may include both smaller strut thickness and a smaller strut width to provide this increased flexibility. The flexing portions can be thought of somewhat as mechanical hinges which provide regions of articulation to the strut assembly. Conversely, the stable portions 38 may include struts having greater strut thickness, and strut width to provide additional strength and added mass to increase the level of radiopacity of the strut assembly 14. As is shown in FIG. 6, there are several areas in which flexing portions 36 are located to provide the increased flexibility needed to maneuver in the patient's vasculature. It should be appreciated that the number, size and location of flexing portions 36 and stable portions 38 of the strut assembly 14 will vary depending upon the particular structure utilized to create the strut assembly.

Figure 8A:
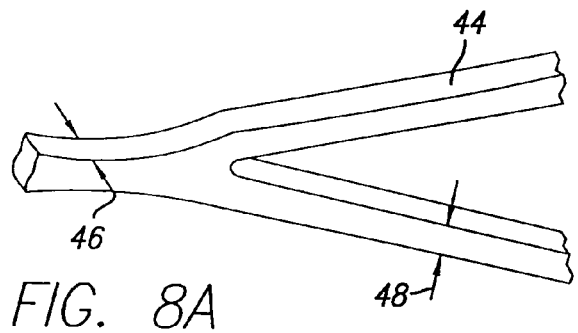
FIG. 8A is an elevational view, partially fragmented, of a strut portion having uniform thickness and width which has been used to form a part of a strut assembly.
Figure 8B:
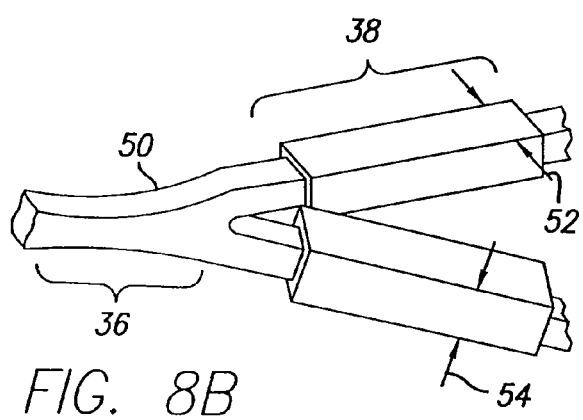
FIG. 8B is an elevational view, partially fragmented, of one embodiment of a strut portion made in accordance with the present invention that can be used to form part of the strut assembly.
Figure 8C:
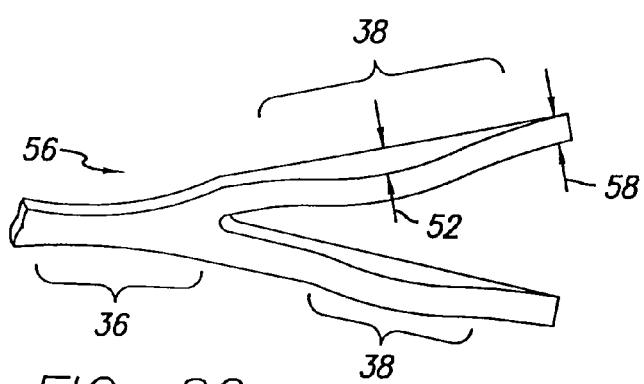
FIG. 8C is an elevational view, partially fragmented, of another embodiment of a strut portion made in accordance with the present invention that can be used to form part of a strut assembly.
Figure 8D:
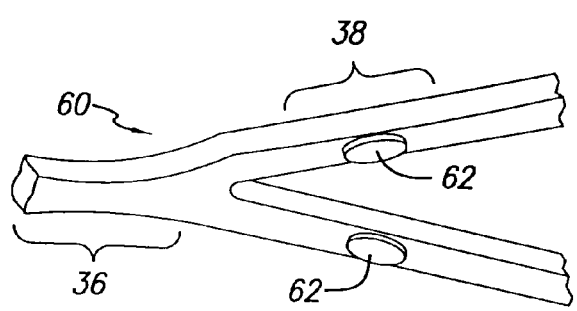
FIG. 8D is an elevational view, partially fragmented, of another embodiment of a strut portion made in accordance with the present invention that can be used to form a part of a strut assembly.

The current invention provides additional strut thickness and/or width to all or part of the stable portions of the strut assembly. FIG. 8A-8D depicts a partially fragmented perspective view of a portion of a strut similar to that shown in FIGS. 6 and 7 which shows different ways of increasing the mass of the strut in the stable portion of the strut assembly. In FIG. 8A, it can be seen that all portions of the strut 44 have the same, or a nominal strut depth 46 and a constant strut width 48. In the embodiment shown in FIG. 8A, there are no stable portions or flex portions due to the fact that the nominal thickness 46 and nominal strut width 48 are substantially uniform throughout. Many prior art filtering devices are made with struts having uniform strut thickness and width. Bending occurs on those devices at points along the strut assembly which are most vulnerable to bending forces. In such devices, there are no specifically formed flexible struts which are designed to flex and bend and take the brunt of the bending forces that can be generated during passage of the device through the patient's vasculature. In FIG. 8B, however, the strut pattern 50 has both stable portions 38 and flexing portions 36. The stable portion 38 is made with a material which has greater than nominal depth 52 and greater than nominal width 54 without compromising the flexibility of the struts in the flexing portion 36. When used on the strut assembly, these thicker and wider struts in the stable portions 38 provide additional strength and enhanced radiopacity characteristics to the strut assembly 14. FIG. 8C depicts a further embodiment of stable portions 38 of a strut 56 having varying strut thickness which smoothly transitions from a nominal strut thickness 46 to a greater-than-nominal thickness 52. In the particular embodiment of FIG. 8C, the strut width 58 is substantially the same. However, due to the greater than nominal strut thickness 52 in the stable portions 38, additional strength and increased radiopacity will be provided to the strut assembly. FIG. 8D provides still another embodiment of a strut portion 60 of a strut assembly in which unique stable portions 38 can be found. In this particular embodiment, the stable portion 38 is made from a geometry which includes a "bump" pattern generating a greater-than-nominal strut thickness 52 in a desired area. The bumps 62 formed in the stable portions 38 would be inherent in the material used to create the strut assembly. Also, in the embodiments shown in FIGS. 8C and 8D, when a restraining sheath is utilized to deploy and retrieve the filter assembly, the variable thickness design effectively reduces the surface area of the strut in contact with sheath, thereby reducing frictional forces which can be generated as the restraining sheath moves over the strut assembly. As a result, the restraining sheath should slide off of the strut assembly with less resistance.

The preparation of a strut assembly in accordance with the present invention can be accomplished in a variety of ways. An initial step would be to select a particular pattern for the struts and identify stable portions and flexing portions. The identification of stable portions can be accomplished using many different techniques. For example, a computer base modeling of a strut pattern can be performed that models the embolic protection device during bending of the strut assembly. Alternatively, a physical model or actual embolic protection device bearing the particular strut pattern could be prepared and subject to bending, so that flexing and stable portions of the strut assembly could be identified through inspection of the physical device. Other approaches for identifying the flexing portions and stable portions would be well-known in the art and are within the scope of the present invention.

After identification of the stable and flexing portions has occurred, a strut assembly can be prepared having the desired strut pattern, with the variations in the strut thickness and/or strut widths associated with the flexing portions and stable portions. Various techniques could be utilized to manufacture the strut assembly. For example, the strut assembly could be prepared from a tubular member having a nominal thickness with the strut pattern being laser cut or otherwise cut to create a rough pattern. Additional material could then be added to the surface of the cut strut pattern on selected stable portions until the selected stable portions reach the desired greater-than-nominal strut depth or greater-than-nominal width, depending again, on the particular pattern which is to be utilized. Various techniques could be used to add the additional material, including sputter coating, electroplating, or chemical vapor deposition.

Figures 9A, 9B, 9C:
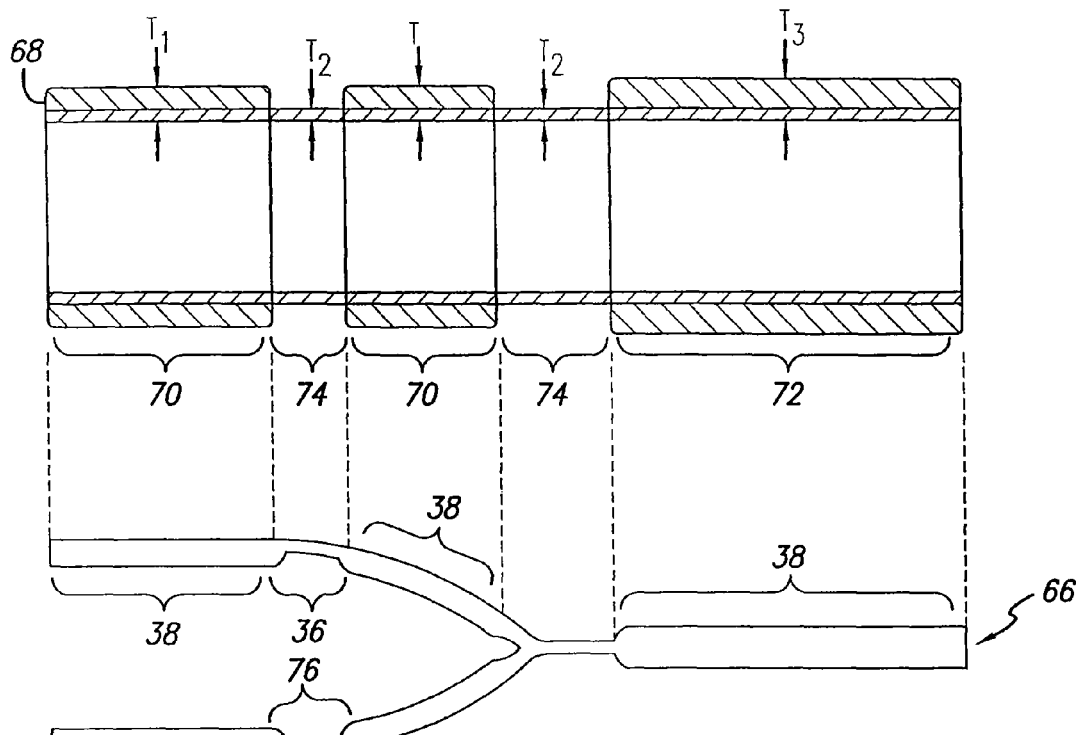
FIG. 9A is an elevational view of a tubular member used to form one particular embodiment of the present invention.
FIG. 9B is an elevational view of one particular strut pattern which can be formed in the tubular member shown in FIG. 9A to create one particular embodiment of a strut assembly made in accordance with the present invention.
FIG. 9C is an elevational view which depicts the wall thickness of the strut pattern shown in FIGS. 9A and 9B taken along line 9C-9C.

Referring now to FIGS. 9A-9C, a particular strut pattern 66 which forms the strut assembly 14, is depicted two-dimensionally (FIG. 9B) as if the strut assembly 14 were cut longitudinally and "unrolled" to form a flat sheet, showing the combination of flex portions 36 and stable portions 38 which, in combination, create the strut assembly 14. FIG. 9A shows a cross-sectional view of a tubular member 68 which could be utilized and laser cut in order to create the varying strut thicknesses of the strut assembly shown in FIG. 9B. As is shown, the tubular member 68 has different wall thicknesses which correspond to the flexing portions 36 and stable portions 38 of the strut assembly 14. The areas 70 which have larger-than-nominal strut thickness in the tubular member are utilized to create the stable regions 38 of the strut assembly. As can be seen in FIGS. 9A and 9C, the wall thicknesses in the areas forming the stable regions 38 can vary. For example, areas 70 have the same wall thickness $T_1$. However, the wall thickness $T_3$ in area 72 forming another stable region has an even greater wall thickness than area 70. This creates an even larger strut thickness in those stable regions of the strut assembly. Area 74, which forms the flexing portions of the strut assembly, has a wall thickness $T_2$ which is less than $T_1$ and $T_3$. Moreover, the width can be increased in those regions as well. In a similar fashion, the strut widths and strut depths in the flexing regions can vary on the strut assembly as well. For example, as can be seen in FIG. 9B, certain strut widths in flexing portions 76 are smaller than the strut widths in the other flexing portions 36. The strut thickness in these areas could also be less-than-nominal strut thickness to provide even increased flexibility. Moreover, the flexing portions can have varying strut thickness, similar to the varying strut thickness of the stable portions 38 depicted in FIG. 8C. For example, in one particular embodiment, the nominal strut thickness can be about 10% or less of the greater-than-nominal strut thickness. In another embodiment, the nominal strut thickness can be about 50% or less of the greater-than-nominal strut thickness. In yet another embodiment, the nominal strut thickness can be about 80% or less of the greater-than-nominal strut thickness. The free ends of the struts could be attached to collars 31, as is shown in FIG. 6, which help form the particular shape of the strut assembly disclosed herein. The free ends 78 of the struts could be attached to the collars using well-known bonding techniques known in the art, including welding, brazing, and adhesive bonding. It should be appreciated that numerous variations of strut width and depths in the various stable and flexing portions of the strut assembly can be achieved in accordance with the present invention.

Due to manufacturing and other considerations, it may be desirable to start with a tubular member having a desired larger than nominal thickness, and then selectively reduce the thickness of desired portions, such as the flexing portions, to create a nominal thickness or even a less-than-nominal thickness. In this particular manner, the tubular member shown in FIG. 9A would have a greater-than-nominal thickness and selected portions of the outer surface would be removed to create the nominal thickness utilized to create the flexing portions of the strut assembly. In the embodiment shown in FIG. 9A, the machining could involve rotating the tubular member along its longitudinal axis, as may be accomplished utilizing a lathe or other rotating device, and pressing a machine tool against the outer surface. Other techniques include chemical etching, laser ablation, grinding, or milling. Once the particular form of the tubular member is selected, the pattern which forms the strut assembly could then be cut into the tubular member. In this manner, the width of the struts in the stable portions could be cut to be larger than the struts in the flexing portions, as is shown in FIG. 9B. Any one of a number of different combinations of stable portions and flexing portions can be utilized, as will be appreciated by those skilled in the art, to create the particular pattern for the strut assembly. Accordingly, a strut assembly will have flexing portions having a nominal thickness and/or nominal strut width, with stable portions having greater than nominal thickness and/or greater than nominal strut widths.

In addition to the physical machining methods discussed above, the reduction in strut thickness could also be achieved through a variety of other methods, including ablating selected surface areas. The ablation could be formed through various methods, including chemical and/or laser ablation. This step may also be formed as part of the process of cutting the strut pattern into the tubular member. For example, where laser cutting is used to cut the strut pattern, the laser might also be used to thin desired portions of the tubular member. Such thinning using a laser might involve changing the focus depth of the laser, changing laser power, or using the laser to tangentially "shave" across the surface of the tubular member thereby removing a layer of material.

The strut assembly of the present invention can be made in many ways. However, the one particular method of making the strut assembly is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser. Prior to laser cutting the strut pattern, the tubular member could be formed with varying wall thicknesses which will be used to create the stable and flexing portions of the strut assembly.

The tubing used to make the strut assembly could possible be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

The strut size is usually very small, so the tubing from which it is made must necessarily also have a small diameter. Typically, the tubing has an outer diameter on the order of about 0.020-0.040 inches in the unexpanded condition. The greater-than-nominal wall thickness of the tubing is usually about 0.076 mm (0.003-0.006 inches). As can be appreciated, the nominal strut depth in the flexing portions will be less. For strut assemblies implanted in body lumens, such as PTA applications, the dimensions of the tubing may be correspondingly larger. While it is preferred that the strut assembly be made from laser cut tubing, those skilled in the art will realize that the strut assembly can be laser cut from a flat sheet and then rolled up in a cylindrical configuration with the longitudinal edges welded to form a cylindrical member.

Generally, the hypotube is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The strut assembly can thus be laser cut much like a stent is laser cut. Details on how the tubing can be cut by a laser are found in U.S. Pat. Nos. 5,759,192 (Saunders) and 5,780,807 (Saunders), which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite finish transformation temperature is between about 0° C. and 20° C. in order to achieve superelasticity. The austenite finish temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding stent made in accordance with the present invention.

The strut assembly of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the strut assembly such that it is super elastic at body temperature. The transformation temperature is at or below body temperature so that the stent is superelastic at body temperature. The strut assembly is usually implanted into the target vessel which is smaller than the diameter if the strut assembly in the expanded position so that the struts apply a force to the vessel wall to maintain the filter element in the expanded position. It should be appreciated that the strut assembly can be made from either superelastic, stress-induced martensite NiTi or shape-memory NiTi.

One way of making the strut assemblies of the present device is to utilize a shape-memory material, such as nickel titanium, which has the struts cut utilizing a machine-controlled laser. A tubular piece of material could be utilized in this process. The strut assembly could be manufactured to remain in its open position while at body temperature and would move to its collapsed position upon application of a low temperature. One suitable method to allow the strut assembly to assume a phase change which would facilitate the strut and filter assembly being mounted into the restraining sheath include chilling the filter assembly in a cooling chamber maintained at a temperature below the martensite finish temperature through the use of liquid nitrogen. Once the strut assembly is placed in its collapsed state, the restraining sheath can be placed over the device to prevent the device from expanding once the temperature is brought up to body temperature. Thereafter, once the device is to be utilized, the restraining sheath is simply retracted to allow the filter assembly/strut assembly to move to its expanded position within the patient's vasculature. If superelastic NiTi is used, the strut assembly/filter assembly can be simply back loaded into the restraining sheath. The strut assembly would be "set" to the expanded position.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology. The perfusion openings can be any different shape or size. A laser, a heated rod or other process can be utilized to create to perfusion openings in the filter material. The holes, would of course be properly sized to catch the particular size of embolic debris of interest. Holes can be lazed in a spiral pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath and recovery sheath can be made from polymeric material such as cross-linked HDPE. These sheaths can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:
1. An embolic filtering device for filtering embolic debris from a patient's vasculature, comprising:
   a filtering assembly including an expandable strut assembly and a filter element attached thereto, the strut assembly including a plurality of struts arranged to create a desired composite strut structure which is adapted to move between a collapsed position and an expanded position, the strut structure including:
   flexing portions which flex when subjected to bending forces that may be developed when the strut assembly is being delivered through the patient's vasculature, the struts forming the flexing portions being made from a first layer of material having a first wall thickness; and
   stable portions that remain relatively stiff when being delivered through the patient's vasculature, the struts forming the stable portions being made from the first layer of material along with a second layer of material having a second wall thickness deposited on the first layer to form a composite wall thickness for the stable portions that is greater than the first wall thickness, wherein each strut has a particular strut width, the strut widths in the stable portions being generally greater than the strut widths in the flexing portions, the strut widths in the flexing portions defining a nominal strut width and the strut width in the stable portions defining a greater-than-nominal strut width.

2. The embolic filtering device of claim 1, wherein the stable portions provide structural strength to maintain the strut assembly in the expanded position.

3. The embolic filtering device of claim 1, wherein flexing portions interconnect adjacent stable portions.

4. The embolic filtering device of claim 1, wherein the flexing portions undergo little or no deformation when subjected to bending forces developed during delivery through the patient's vasculature.

5. The embolic filtering device of claim 4, wherein the flexing portions are made from a material which is self-expanding.

6. The embolic filtering device of claim 1, wherein the struts are made from a material which is self-expanding.

7. The embolic filtering device of claim 6, wherein the material is nickel-titanium.

8. The embolic filtering device of claim 1, wherein the strut thickness in the flexing portions define a nominal strut thickness and the strut thickness in the stable portions define a greater-than-nominal strut thickness.

9. The embolic filtering device of claim 8, wherein the nominal strut thickness is about 10% or less of the greater-than-nominal strut thickness.

10. The embolic filtering device of claim 8, wherein the nominal strut thickness is about 50% or less of the greater-than-nominal strut thickness.

11. The embolic filtering device of claim 8, wherein the nominal strut thickness is about 80% or less of the greater-than-nominal strut thickness.

12. The embolic filtering device of claim 8, wherein some of the flexing portions have less than nominal strut thickness.

13. The embolic filtering device of claim 8, wherein some flexing portions have strut thickness different from other flexing portions but less than the strut thickness in the stable portions.

14. The embolic filtering device of claim 8, wherein each strut has a particular strut width, the strut widths in the stable portions being generally greater than the strut widths in the flexing portions.

15. The embolic filtering device of claim 14, wherein the strut widths in the flexing portions define a nominal strut width and the strut width in the stable portions define a greater-than-nominal strut width.

16. The embolic filtering device of claim 1, wherein some of the flexing portions have less than nominal strut widths.

17. The embolic filtering device of claim 16, wherein some flexing portions have strut widths different from other flex portions but less than the strut widths in the stable portions.

* * * * *